(12) United States Patent
Sakata et al.

(10) Patent No.: US 8,420,006 B2
(45) Date of Patent: Apr. 16, 2013

(54) METHOD OF MANUFACTURING TRANSLUCENT CERAMIC AND ORTHODONTIC MEMBER

(75) Inventors: Masaaki Sakata, Hachinohe (JP);
Junichi Hayashi, Hachinohe (JP);
Hideki Ishigami, Hachinohe (JP)

(73) Assignee: Seiko Epson Corporation, Tokyo (JP)

( * ) Notice: Subject to any disclaimer, the term of this patent is extended or adjusted under 35 U.S.C. 154(b) by 367 days.

(21) Appl. No.: 12/397,516

(22) Filed: Mar. 4, 2009

(65) Prior Publication Data
US 2009/0224442 A1 Sep. 10, 2009

(30) Foreign Application Priority Data
Mar. 5, 2008 (JP) ................. 2008-055520

(51) Int. Cl.
*B28B 1/24* (2006.01)
*C04B 33/32* (2006.01)
*A61C 13/20* (2006.01)

(52) U.S. Cl.
USPC ............................. 264/656; 264/16

(58) Field of Classification Search ............ 264/16, 264/910, 656, 657
See application file for complete search history.

(56) References Cited

U.S. PATENT DOCUMENTS

| | | | | |
|---|---|---|---|---|
| 2,492,483 A | * | 12/1949 | Keene | 249/67 |
| 3,932,085 A | * | 1/1976 | Horbach | 425/186 |
| 4,545,155 A | * | 10/1985 | Nakata | 451/39 |
| 4,783,297 A | * | 11/1988 | Ito et al. | 264/645 |
| 4,954,080 A | * | 9/1990 | Kelly et al. | 433/8 |
| 5,091,346 A | * | 2/1992 | Inoue et al. | 501/93 |

(Continued)

FOREIGN PATENT DOCUMENTS

| | | |
|---|---|---|
| JP | 05-042170 | 2/1993 |
| JP | 05-043307 | 2/1993 |

(Continued)

OTHER PUBLICATIONS

JP 05-042170 A (Enboku, Masakazu) Feb. 23, 1993 (English language machine translation of foreign patent already of record on applicant's IDS dated Mar. 5, 2010). [online][retrieved Nov. 2, 2010]. Retrieved from: Japan Patent Office Advanced Industrial Property Network.*

(Continued)

*Primary Examiner* — Joseph Del Sole
*Assistant Examiner* — Erin Snelting

(57) ABSTRACT

A method of manufacturing a translucent ceramic is provided. The method comprises: mixing a raw powder and an organic binder and kneading them to obtain a compound, the raw powder containing an aluminum oxide powder and a magnesium oxide powder, and the organic binder containing a first organic component and a second organic component; molding the compound in a predetermined shape by an injection molding method to obtain a green body; debinding the organic binder contained in the green body to obtain a brown body; and sintering the brown body to obtain a sintered body of the translucent ceramic. When the softening point of the first organic component is defined as "$T_1$" (° C.) and the softening point of the second organic component is defined as "$T_2$" (° C.), the kneading step is carried out at a temperature in the range of $T_2$ or higher but lower than $T_1$ after the raw powder and the organic binder are preheated at a temperature in the range of $T_1$ to $T_1+100$(° C.). An orthodontic member is also provided.

16 Claims, 6 Drawing Sheets

U.S. PATENT DOCUMENTS

| | | | |
|---|---|---|---|
| 5,432,224 A * | 7/1995 | Ryuhgoh et al. | 524/439 |
| 6,306,788 B1 | 10/2001 | Watanabe et al. | |
| 2001/0049412 A1 | 12/2001 | Seyama et al. | |

FOREIGN PATENT DOCUMENTS

| JP | 07-126060 | 5/1995 |
| JP | 2002-029856 | 1/2002 |
| JP | 2003-095728 | 4/2003 |
| JP | 2004-216663 | 8/2004 |
| JP | 3783445 | 3/2006 |

OTHER PUBLICATIONS

Wu, Rong-Yuan et al., "De-Agglomeration Kinetics of Feedstocks With Granule Tetragonal Zirconia Polycrystalline Powder", Journal of American Ceramic Society, 2005, pp. 1734-1739.

Yang, S. Y. et al., "Kneading and Molding of Ceramic Microparts by Precision Powder Injection Molding (PIM)", Journal of Applied Polymer Science, 2006, pp. 892-900.

* cited by examiner

METHOD OF MANUFACTURING TRANSLUCENT CERAMIC AND ORTHODONTIC MEMBER

CROSS-REFERENCE TO RELATED APPLICATION

This application claims a priority to Japanese Patent Application No. 2008-055520 filed on Mar. 5, 2008 which is hereby expressly incorporated by reference herein in its entirety.

BACKGROUND

1. Technical Field

The present invention relates to a method of manufacturing a translucent ceramic and an orthodontic member, more specially relates to a method of manufacturing a translucent ceramic and an orthodontic member using the translucent ceramic manufactured by the method.

2. Related Art

There has been industrially used a translucent alumina (translucent aluminum oxide) sintered body that makes use of specific properties of ceramics superior in translucency, weather resistance and hardness.

In general, the translucent alumina sintered body is manufactured in the following manner. First, an alumina powder, a sintering agent and an organic binder are mixed together to obtain a mixture. Thereafter, the mixture is put into a mold and then molded by a press molding method, an injection molding method or other molding methods to obtain a green body. A sintered body, that is, the translucent alumina sintered body is obtained by debinding and sintering the green body (Japanese Patent No. 3783445 is an example of the related art.).

The thus obtained translucent alumina sintered body is constituted of polycrystalline alumina and therefore contains a multiplicity of crystal grains.

The translucency of the translucent alumina sintered body depends on a state of the crystal grains. More specifically, if a size of the crystal grains is generally uniform throughout the translucent alumina sintered body, the translucent alumina sintered body exhibits high translucency.

However, a size of crystal grains is ununiform according to a conventional manufacturing method. This poses a problem in that a translucent alumina sintered body obtained by the conventional manufacturing method shows reduced translucency and mechanical properties. Presence of pores in the translucent alumina sintered body is one of factors causing the reduction in translucency.

SUMMARY

It is an object of the present invention to provide a method of manufacturing a translucent ceramic being capable of manufacturing a translucent ceramic sintered body that exhibits high and uniform translucency and has a shape close to a desired one, and an orthodontic member with good sensuousness using the translucent ceramic manufactured by such a method.

This object is achieved by the present invention described below.

One aspect of the present invention is directed to a method of manufacturing a translucent ceramic. The method comprises: mixing a raw powder and an organic binder and kneading them to obtain a compound, the raw powder containing an aluminum oxide powder and a magnesium oxide powder, and the organic binder containing a first organic component and a second organic component of which decomposition temperature and softening point are lower than a decomposition temperature and a softening point of the first organic component, respectively; molding the compound in a predetermined shape by an injection molding method to obtain a green body; debinding the organic binder contained in the green body to obtain a brown body; and sintering the brown body to obtain a sintered body of the translucent ceramic.

When the softening point of the first organic component is defined as "$T_1$" (° C.) and the softening point of the second organic component is defined as "$T_2$" (° C.), the kneading step is carried out at a temperature in the range of $T_2$ or higher but lower than $T_1$ after the raw powder and the organic binder are preheated at a temperature in the range of $T_1$ to $T_1+100$(° C.).

This makes it possible to manufacture a sintered body of the translucent ceramic, that is, a translucent ceramic sintered body that exhibits high and uniform translucency and has a shape close to a desired one.

In the method of manufacturing the translucent ceramic according to the present invention, it is preferred that a content of the magnesium oxide powder contained in the raw powder is in the range of 0.01 to 0.15% by mass.

This makes it possible to sufficiently prevent growth of aluminum oxide crystal grains and formation of pores in grain boundaries without causing segregation of magnesium oxide. Therefore, it is possible to manufacture a translucent ceramic sintered body with high density and increased translucency.

In the method of manufacturing the translucent ceramic according to the present invention, it is also preferred that a content of the raw powder in the mixing step is in the range of 30 to 70% by volume.

This ensures that the compound has good flowability even though it contains the raw powder at a relatively high percentage. Therefore, it is possible to improve filling efficiency of the compound into a mold of an injection molding device in an injection molding process, eventually providing a translucent ceramic sintered body that exhibits high density (compactness) and has a shape close to a desired one (namely, a near net shape).

In the method of manufacturing the translucent ceramic according to the present invention, it is also preferred that the first organic component includes at least one of polystyrene and ethylene-vinyl acetate copolymer.

These materials serve to increase bonding strength in the green body and can reliably prevent the green body from becoming susceptible to deformation. In addition, these materials are easily decomposed by heat despite relatively high flowability thereof and therefore can be debound with ease. This makes it possible to easily and reliably debind the organic binder contained in the green body while keeping its shape intact.

In the method of manufacturing the translucent ceramic according to the present invention, it is also preferred that the second organic component includes a paraffin wax.

The paraffin wax is particularly useful as the second organic component, because it exhibits particularly high flowability when softened and superior pyrolyzability.

In the method of manufacturing the translucent ceramic according to the present invention, it is also preferred that a content of the second organic component contained in the organic binder is in the range of 10 to 50% by mass.

This makes it possible to optimize a viscosity of the compound in its mixing and kneading processes and to make highly compatible dispersibility and flowability of the raw powder and the organic binder. As a result, it is possible to obtain a green body in which the raw powder and the organic binder are homogeneously mixed and to which a shape of a cavity of the mold is faithfully transferred.

In the method of manufacturing the translucent ceramic according to the present invention, it is also preferred that the kneading step is successively carried out without having to cool the raw powder and the organic binder to below the softening point of the second organic component after completion of the preheating.

This makes it possible to prevent occurrence of problems attendant on the cooling. Examples of such problems include: the first and second organic components becoming susceptible to separation and the organic binder suffering from reduction in homogeneity, which would arise from the cooling of the preheated organic binder.

In the method of manufacturing the translucent ceramic according to the present invention, it is also preferred that the debinding step is carried out under debinding conditions that a debinding temperature is in the range of 400 to 600° C. and a debinding time is in the range of 1 to 20 hours.

This makes it possible to reliably debind the organic binder having a typical composition. Furthermore, the green body is prevented from being explosively debound, which makes it possible to prevent occurrence of cracks in the green body and sharp reduction in dimensional accuracy of the green body.

In the method of manufacturing the translucent ceramic according to the present invention, it is also preferred that the sintering step is carried out under sintering conditions that a sintering temperature is in the range of 1600 to 1900° C. and a sintering time is in the range of 0.5 to 8 hours.

This makes it possible to reliably sinter the brown body while preventing remarkable growth of the crystal grains.

In the method of manufacturing the translucent ceramic according to the present invention, it is also preferred that the method further comprises subjecting the green body having a surface to a surface treatment between the molding step and the debinding step, wherein the surface treatment is carried out by injecting resin particles onto the surface of the green body.

This makes it possible to subject the green body to a surface treatment through which to remove impurities existing on the surface of the green body. As a result, it is possible to prevent the impurities from remaining on the surface of the finally obtained translucent ceramic sintered body. It is also possible to remove burrs generated in the green body.

In the method of manufacturing the translucent ceramic according to the present invention, it is also preferred that the resin particles are decomposable in the debinding step.

This makes it possible to decompose and remove the resin particles in the debinding step, even if the resin particles adhere to the surface of the green body when they are injected toward the surface of the green body. Therefore, it is possible to prevent the resin particles from remaining in the surface of the translucent ceramic sintered body and to prevent deterioration in translucency of the translucent ceramic sintered body.

In the method of manufacturing the translucent ceramic according to the present invention, it is also preferred that an average particle size of the resin particles is in the range of 50 to 500 μm.

This makes it possible to reliably remove the impurities adhering to the surface of the green body, while preventing notable growth of grinding marks formed on the surface of the green body by impingement of the resin particles. As a result, it is possible to prevent notable irregularities or impurities from remaining on the surface of the translucent ceramic sintered body and to produce a translucent ceramic sintered body with superior translucency.

In addition, it is possible to optimize mass of the resin particles, i.e., impact energy applied to the green body. This makes it possible to prevent serious reduction in dimensional accuracy of the green body.

In the method of manufacturing the translucent ceramic according to the present invention, it is also preferred that the resin particles are constituted of unsaturated polyester as a main component thereof.

Since the resin particles mainly constituted of the unsaturated polyester exhibit optimal hardness relative to the hardness of the surface of the green body, it is possible to quite reliably grind only an outermost surface layer of the green body. It is also possible to reliably decompose and remove the resin particles in the debinding step.

In the method of manufacturing the translucent ceramic according to the present invention, it is also preferred that the injection molding method uses a mold, the mold has an inner surface and a cavity defined by the inner surface, and Vickers hardness HV of the inner surface of the mold is 800 or more.

This makes it possible to restrain the inner surface defining the cavity from being damaged or worn out by friction with the compound in the molding and kneading steps. As a result, it is possible to restrain the scars or the like otherwise left on the inner surface defining the cavity from being transferred to the green body.

Eventually, it is possible to restrain creation of irregularities on the surface of the translucent ceramic sintered body. This provides a translucent ceramic sintered body with increased translucency.

In the method of manufacturing the translucent ceramic according to the present invention, it is also preferred that a surface roughness Ra of the inner surface of the mold is 0.8 μm or less.

This makes a sufficiently smooth surface of the green body, eventually providing a translucent ceramic sintered body with a smooth surface. In terms of a wavelength of light, the surface roughness Ra falling within the above-noted range is effective in providing a translucent ceramic sintered body that allows visible rays to sufficiently pass therethrough.

In case where an orthodontic member is produced using the translucent ceramic sintered body mentioned above, a color of teeth can be sufficiently visible through the orthodontic member. Therefore, there is provided an orthodontic member with good sensuousness.

In method of manufacturing the translucent ceramic according to the present invention, it is also preferred that the mold has the cavity having a predetermined shape, and ejector pins provided for insertion into and extraction from the cavity and configured to push out the green body formed by the mold from the cavity, wherein each of the ejector pins has a surface to push the green body and the inner surface of the mold includes a bottom surface, wherein in a state that the mold is closed, a step difference between the bottom surface of the inner surface of the mold and the surface of each of the ejector pins is 0.05 mm or less.

This ensures that a step difference possibly formed on the surface of the translucent ceramic sintered body by the ejector pins is controlled small enough not to greatly affect the translucency of the translucent ceramic sintered body.

Another aspect of the present invention is directed to an orthodontic member manufactured by the method of manufacturing the translucent ceramic described above.

The translucent ceramic, that is, the orthodontic member thus manufactured enjoys good sensuousness.

DESCRIPTION OF EXEMPLARY EMBODIMENTS

Hereinafter, a method of manufacturing a translucent ceramic and an orthodontic member using the translucent ceramic manufactured by the method in accordance with the present invention will be described in detail with reference to the accompanying drawings.

The method of manufacturing the translucent ceramic o f the present invention is capable of manufacturing a translucent ceramic sintered body that exhibits superior translucency and mechanical properties and has a shape close to a desired one.

The translucent ceramic sintered body manufactured by the present method is applicable to various kinds of products, such as an arc tube for discharge lamps, a component part for chemical processing devices (e.g., a chamber, a stage, a support tool or a window member), an orthodontic member, a prosthetic tooth, eating utensils and jewelry goods.

For the purpose of illustration, a description will be made herein below on a method of manufacturing an orthodontic bracket (or an orthodontic member) using the method of manufacturing the translucent ceramic of the present invention.

Figure 1:
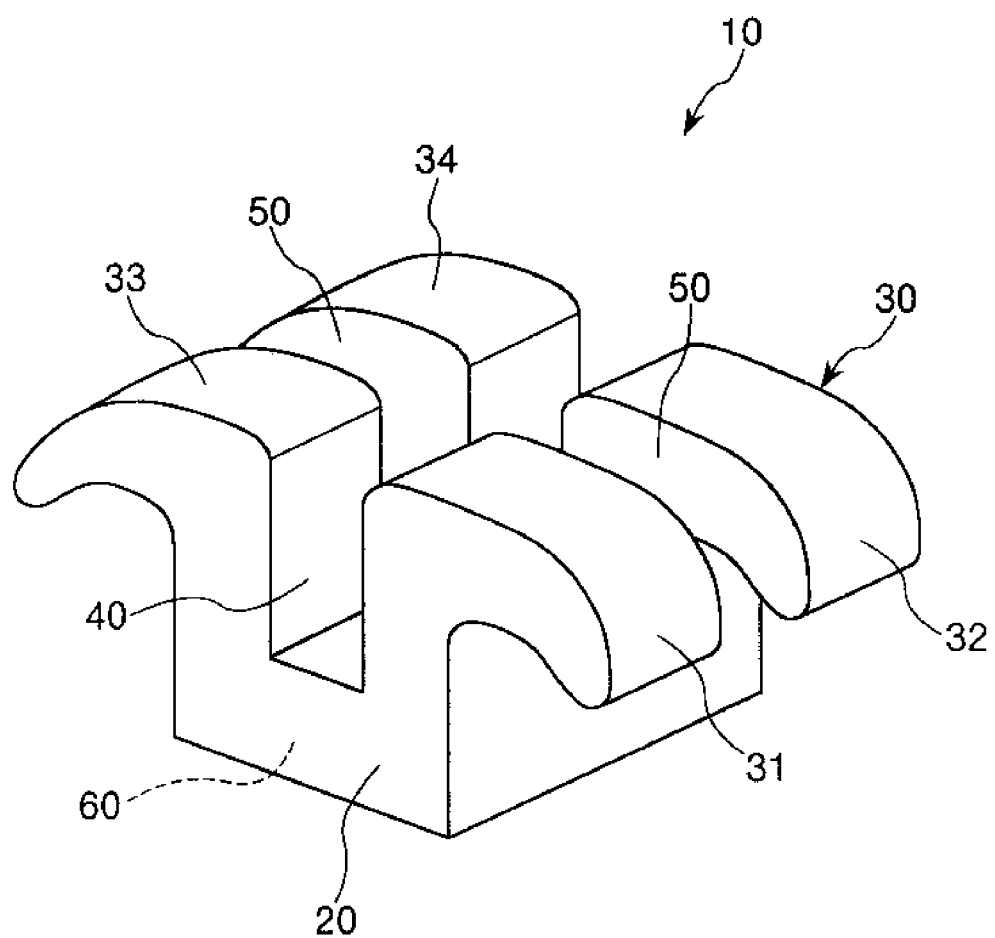
FIG. 1 is a perspective view showing an orthodontic bracket to which an orthodontic member according to the present invention is applied.

FIG. 1 is a perspective view showing an orthodontic bracket to which an orthodontic member according to the present invention is applied.

The orthodontic bracket (hereinafter simply referred to as "bracket") 10 shown in FIG. 1 includes a planar base (or a bracket base or a bracket stem) 20 and an engaging portion (or a tie wing) 30 formed to protrude from the base 20.

In a central region of the engaging portion 30, there is formed a slit (or a groove) 40 in which a wire not shown is inserted.

Another slit (or another groove) 50 intersecting the slit 40 is formed in the engaging portion 30. The engaging portion 30 is divided by the slits 40 and 50 into two pairs of arc-shaped protrusions 31, 32, 33 and 34 extending outwards.

In the present embodiment, each of the slits 40 and 50 has a rectangular cross-section. However, the cross-section of each of the slits 40 and 50 is not limited thereto but may have, e.g., a V-like shape or a U-like shape.

When the bracket 10 is in use, the lower (rear) surface 60 of the base 20 is fixed to teeth by an adhesive agent or other fixing means. Therefore, if the bracket 10 is attached to the front surfaces of the teeth, a color of the teeth is turned to a color exhibited by the bracket 10.

In this regard, it is desirable that the bracket 10 does not mar visual impression of a tooth row and the presence thereof is hardly recognizable. From this point of view, the color exhibited by the bracket 10 is preferably the same as the color of the teeth and, more preferably, substantially transparent (or translucent).

With the method of manufacturing the translucent ceramic of the present invention to be described below, it is possible to easily manufacture the bracket (translucent ceramic or translucent ceramic sintered body) 10 superior in translucency and hardness.

Next, a description will be made on a method of manufacturing the bracket 10 using the method of manufacturing the translucent ceramic of the present invention.

Figure 2:
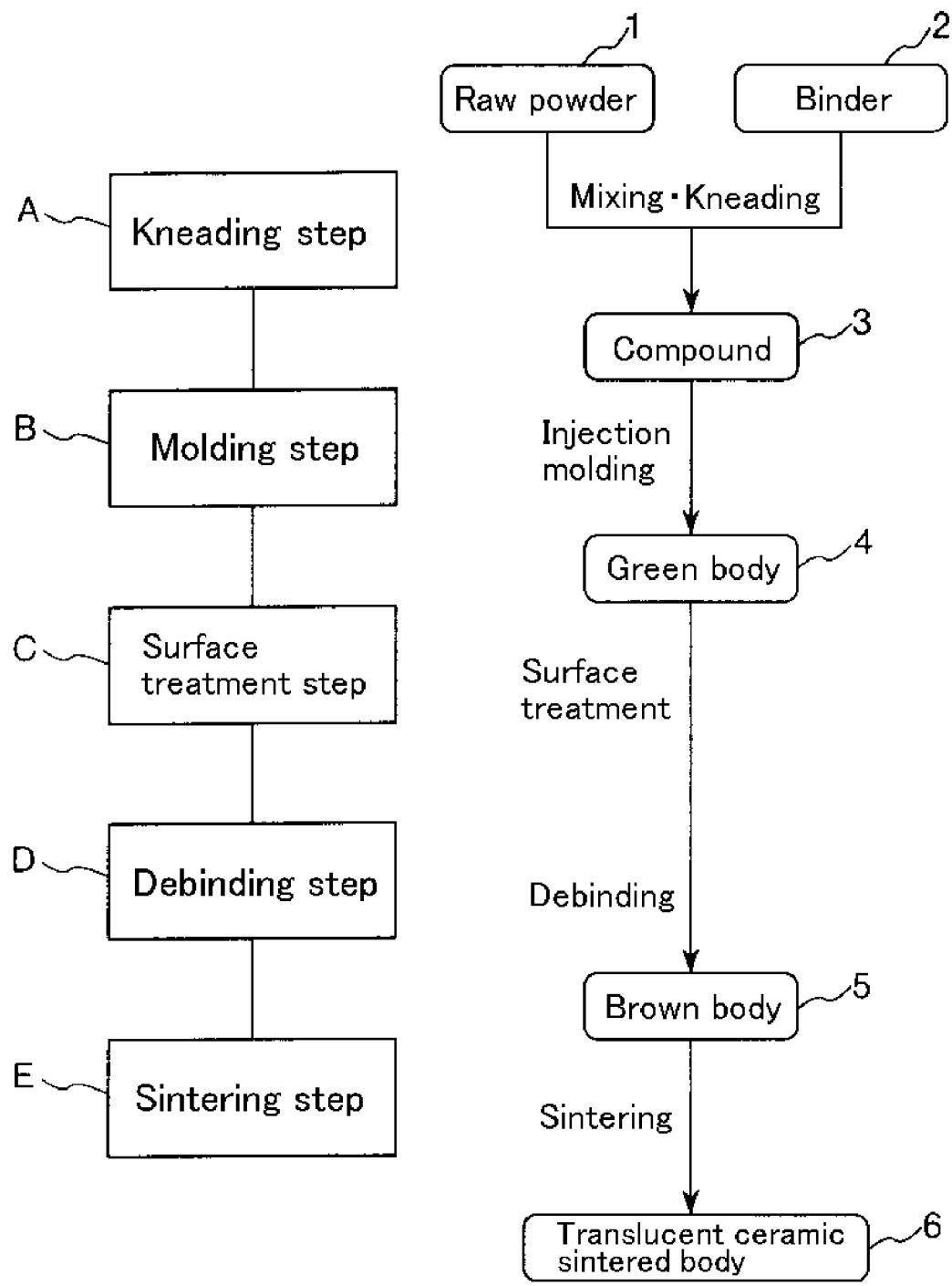
FIG. 2 is process diagrams illustrating one embodiment of a method of manufacturing the orthodontic bracket using a method of manufacturing a translucent ceramic according to the present invention.
Figure 3:
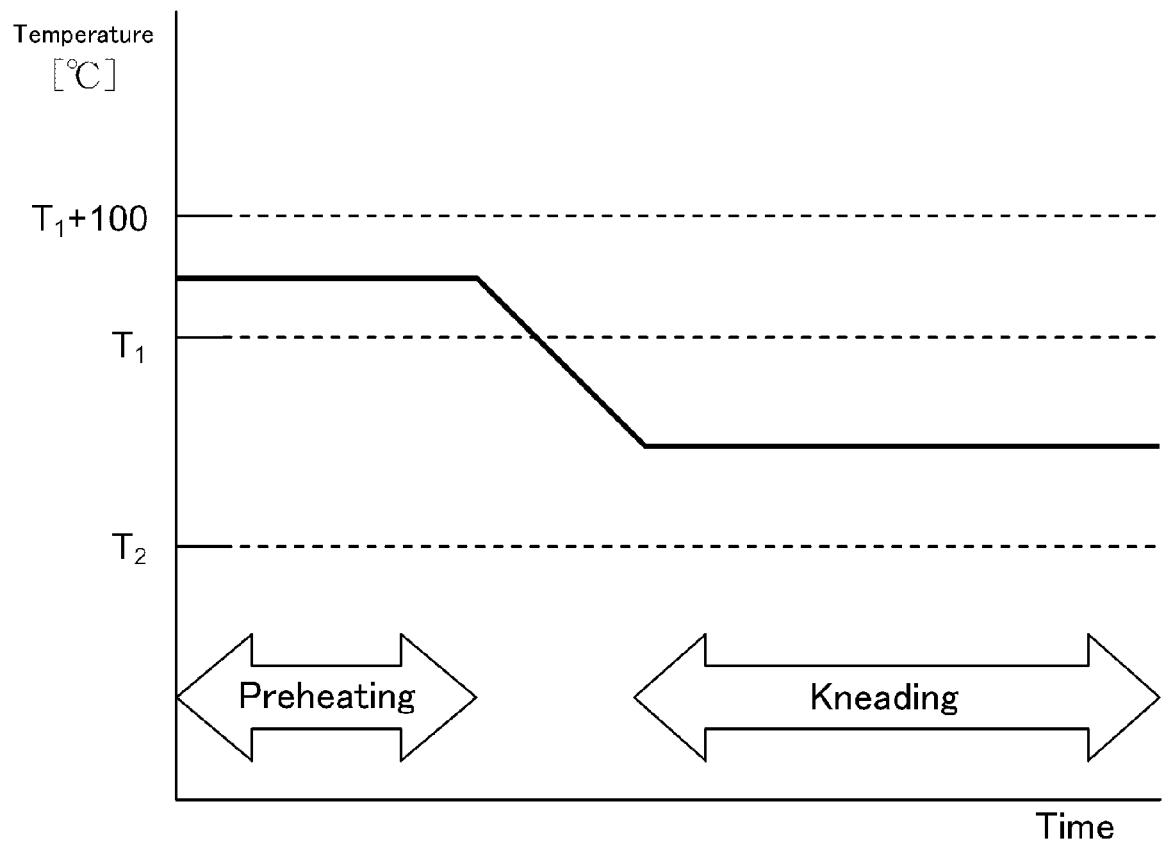
FIG. 3 is a graph representing a temperature profile in mixing and kneading steps.

FIG. 2 is process diagrams illustrating one embodiment of a method of manufacturing the bracket (an orthodontic bracket) using the method of manufacturing the translucent ceramic of the present invention. FIG. 3 is a graph representing a temperature profile in mixing and kneading steps.

The method of manufacturing the a bracket illustrated in FIG. 2 includes [A] a kneading step of kneading a composition formed of a raw material to obtain a compound, [B] a molding step of molding the compound obtained in the kneading step by an injection molding method to obtain a green body, [C] a surface treatment step of injecting resin particles toward the surface of the green body thus obtained, [D] a debinding step of debinding the green body subjected to the surface treatment to obtain a brown body and [E] a sintering step of sintering the brown body thus obtained to obtain a sintered body of the bracket (hereinafter, simply referred to as "translucent ceramic sintered body").

A: Mixing and Kneading Steps

A-1: Prior to describing the kneading step, a description will be made first on a composition used as a raw material of the bracket 10 (a translucent ceramic). The composition contains a raw powder 1 and an organic binder 2. Hereinafter, the respective ingredients of the composition will be described in detail.

(a) Raw Powder

The raw powder 1 is used as the raw material of the translucent ceramic. In the present invention, the raw powder 1 includes an aluminum oxide powder and a magnesium oxide powder.

Among them, the aluminum oxide powder is used as a major component of the translucent ceramic. The aluminum oxide powder is divided into a powder with a crystal structure of $\alpha$-$Al_2O_3$ (corundum) and a powder with a crystal structure of $\gamma$-$Al_2O_3$, the former of which is preferably used.

On the other hand, the magnesium oxide powder acts to prevent growth of crystal grains and formation of pores in grain boundaries when the aluminum oxide powder is sintered in the below-mentioned sintering step.

The content of the magnesium oxide powder included in the raw powder 1 is preferably in the range of about 0.01 to 0.15% by mass and more preferably in the range of about 0.03 to 0.10% by mass. By ensuring that the content of the magnesium oxide powder falls within the above-noted range, it is possible to obtain the translucent ceramic with high density and increased translucency. In other words, it is possible to obtain a translucent ceramic sintered body 6 with high density and increased translucency.

If the content of the magnesium oxide powder is smaller than the lower limit value noted above, the action of the magnesium oxide powder becomes insufficient, which may possibly make it impossible to increase density and translucency of the translucent ceramic sintered body 6. In contrast, if the content of the magnesium oxide powder is greater than the upper limit value noted above, the translucency may be sharply reduced by segregation of magnesium oxide or other causes.

An average particle size of the raw powder 1 is not particularly limited to a specific value but may be preferably in the range of about 0.3 to 10 µm and more preferably in the range of about 0.5 to 5 µm. By ensuring that the average particle size of the raw powder 1 falls within the above-noted range, it is possible to obtain a green body 4 with high density.

Furthermore, the translucent ceramic sintered body 6 obtained by debinding and sintering the green body 4 is rendered superior in translucency and mechanical strength. In the present invention, the term "average particle size" refers to a particle size of a powder distributed at the 50% cumulative volume point in a particle size distribution.

The content of the raw powder 1 contained in the composition is not particularly limited to a specific value but may be preferably in the range of about 30 to 70% by volume and more preferably in the range of about 40 to 60% by volume. By ensuring that the content of the raw powder 1 falls within the above-noted range, the compound 3 obtained by kneading the composition (raw powder and organic binder) has good flowability even though it contains the raw powder 1 at a relatively high percentage.

Therefore, it is possible to improve filling efficiency of the compound 3 into a mold in the injection molding method, eventually providing a translucent ceramic sintered body 6 that exhibits high density (compactness) and has a shape close to a desired one (namely, a near net shape).

In addition, the raw powder 1 may contain additives such as a sintering agent and the like. Examples of the sintering agent include compounds such as oxide, nitrate, acetate, hydroxide and chloride of such elements as scandium, yttrium, zirconium, hafnium and lanthanum.

(b) Organic Binder

The organic binder 2 is an organic component that contributes to moldability (ease of molding) of the compound 3 and shape stability (shape retention) of the green body 4 in the below-mentioned molding step. Inclusion of such an organic component (organic binder 2) in the composition makes it possible to easily and reliably produce a translucent ceramic sintered body 6 superior in dimensional accuracy.

The organic binder 2 used in the present invention includes a first organic component and a second organic component lower in a decomposition temperature and a softening point than the first organic component.

Among them, the first organic component acts to increase viscosity of the compound 3 during the kneading process. This makes it possible to apply a shear force to the compound 3 during the kneading process. Therefore, use of the first organic component makes it possible to homogeneously disperse the raw powder 1 and the organic binder 2 in the compound 3.

Examples of the first organic component include polyethylene, polypropylene, ethylene-vinyl acetate copolymer, polystyrene, polymethyl methacrylate, polybutyl methacrylate, polyamide, polyethylene terephthalate, polybutylene terephthalate, polyvinyl alcohol, copolymers thereof and the like, one or more of which can be used independently or in combination.

Among them, at least one of polystyrene and ethylene-vinyl acetate copolymer is preferably used as the first organic component. These components serve to increase bonding strength in the green body 4 and can reliably prevent the green body 4 from becoming susceptible to deformation.

In addition, these components (organic binder 2) are easily decomposed by a heat despite the relatively high flowability thereof and therefore can be debound with ease. This makes it possible to easily and reliably debind the green body 4 containing these components, while keeping its shape intact.

On the other hand, the second organic component acts to impart flowability to the compound 3 during the kneading process and to increase shape transferability in the molding process. Therefore, use of the second organic component makes it possible to easily and reliably produce a translucent ceramic sintered body 6 with enhanced dimensional accuracy.

A n organic component having a decomposition temperature and a softening point lower than those of the first organic component may be used as the second organic component. Examples of the second organic component include paraffin wax, microcrystalline wax, oxidized wax, ester wax, low molecular weight polyethylene and the like, one or more of which can be used independently or in combination.

Among them, paraffin wax is preferably used as the second organic component. Since paraffin wax shows particularly high flowability when softened and is superior in pyrolyzability, it is particularly suitable for use as the second organic component.

In case where the first and second organic components have no softening point, the melting points thereof may be regarded as their softening points. For example, if the second organic component has no softening point, an organic component having a melting point lower than the softening point of the first organic component may be used as the second organic component.

The content of the second organic component contained in the organic binder 2 is preferably in the range of about 10 to 50% by mass and more preferably in the range of about 15 to 45% by mass. By ensuring that the content of the second organic component falls within the above-noted range, it is possible to optimize viscosity of the compound 3 in its kneading process and to make highly compatible dispersibility and flowability of the raw powder 1 and the organic binder 2.

This makes it possible to obtain a green body 4 in which the raw powder 1 and the organic binder 2 are homogeneously mixed and to which a shape of a cavity of the mold is faithfully transferred.

The composition described above may contain an additive as well as (a) the raw powder 1 and (b) the organic binder 2. Examples of such an additive include a dispersant (lubricant), a plasticizer and the like, one or more of which can be used independently or in combination.

Examples of the dispersant include: a higher fatty acid such as stearic acid, distearic acid, tristearic acid, linolenic acid, octane acid, oleic acid, palmitic acid, naphthene acid and the like; an anionic organic dispersant such as polyacrylic acid, polymethacrylic acid, polymaleic acid, acrylic acid-maleic acid copolymer, polystyrene sulfonic acid and the like; a cationic organic dispersant such as a quaternary ammonium base and the like; a nonionic organic dispersant such as carboxymethyl cellulose, polyethylene glycol and the like; and an inorganic dispersant such as tricalcium phosphate and the like.

Examples of the plasticizer include phthalate ester (e.g., DOP, DEP or DBP), adipic acid ester, trimellitic acid ester, sebacic acid ester and the like.

A-2: Next, the afore-mentioned ingredients are mixed and kneaded to obtain a compound 3.

A-2a: First, the composition is preheated at a specified temperature. As illustrated in FIG. 3, the preheating temperature is preferably in the range of $T_1$ to $T_1+100°$ C., where the $T_1$ is the softening point (° C.) of the first organic component contained in the organic binder 2 and the $T_2$ is the softening point (° C.) of the second organic component contained in the organic binder 2.

The first and second organic components are usually mixed in a powdery form and softened through the preheating process performed in the above-noted temperature range. Thus the first and second organic components are rendered easy to enter between the particles of the raw powder 1, which makes it possible to restrain pores from remaining in the compound 3. As a result, a translucent ceramic sintered body 6 with high density is obtained at last.

The preheating process performed in the above-noted temperature range helps increase affinity of the first and second organic components for the raw powder 1. Consequently, it is possible to increase mutual dispersibility of the first and second organic components and the raw powder 1 in the kneading process performed after the preheating process.

If the preheating temperature is lower than the lower limit value noted above, it becomes impossible to soften the first organic component through the preheating process, which leads to failure to provide the actions and effects set forth above. In contrast, if the preheating temperature is higher than the upper limit value noted above, the second organic component is softened beyond necessity and separated.

This may possibly reduce the effects provided by the organic binder 2. The preheating temperature is preferably in the range of $T_1$ to $T_1+50°$ C. It is preferred that the preheating time is for a length of time from about 5 to 60 minutes.

A-2b: Next, the preheated composition is subjected to kneading. As can be seen in FIG. 3, the kneading temperature is set equal to or higher than $T_2$ but lower than $T_1$. Through the kneading process performed in this temperature range, only the second organic component contained in the composition is melted or softened, with the first organic component being hardly melted or softened.

Inclusion of the first organic component in a solid state allows the compound 3 to have a moderate high viscosity, which makes it possible to exert a great enough shear force on the compound 3. This increases mutual dispersibility of the raw powder 1 and the organic binder 2, thus ensuring that the compound 3 becomes homogeneous.

This also increases mutual dispersibility of the aluminum oxide powder and the magnesium oxide powder contained in the raw powder 1, thereby allowing the aluminum oxide powder and the magnesium oxide powder to be distributed evenly. As a result, it is possible to reduce occurrence of uneven debinding in the below-mentioned debinding step and occurrence of uneven sintering in the below-mentioned sintering step, eventually providing a translucent ceramic sintered body 6 that exhibits high density and increased translucency.

The preheating process as set forth above improves flowability of the compound 3, thus allowing the compound 3 to be spread into every hole and corner of the cavity of the mold in the below-mentioned molding step. This makes it possible to further enhance the shape transferability in the molding process.

If the kneading temperature is lower than the lower limit value noted above, it becomes impossible to soften the second organic component. Thus the compound 3 is given no flowability, which makes it impossible to knead the composition. In contrast, if the kneading temperature is higher than the upper limit value noted above, the first organic component as well as the second organic component is softened to thereby reduce the viscosity of the organic binder 2 as a whole.

In this state, it is impossible to apply a great enough shear force to the compound 3 (to sufficiently transfer a stirring force to the compound 3), which results in insufficient kneading. As a consequence, it becomes impossible to fully disperse the aluminum oxide powder and the magnesium oxide powder in the composition, which leads to partial growth of crystal grains.

A kneading time is preferably for a length of time from about 15 to 210 minutes. Just like the mixing process, the kneading process may be performed in any atmosphere. However, it is preferred that the kneading process is carried out at a vacuum pressure or a reduced pressure (e.g., at 3 kPa or less) or in a non-oxidative atmosphere, e.g., in an atmosphere of inert gas such as a nitrogen gas, an argon gas, a helium gas or the like.

The composition kneading operation can be performed by various kinds of kneading machines including a pressing kneader type or double-arm kneader type kneading machine, a roll type kneading machine, a banbury type kneading machine, a single-shaft or double-shaft extruding and kneading machine, and the like.

It is particularly preferable to use the double-shaft extruding and kneading machine. The reason is that the double-shaft extruding and kneading machine can apply a great enough shear force to the composition and therefore can reliably perform the kneading process even if the composition has increased viscosity.

It is preferred that a ceramic is coated on the inner surface of a kneading vessel or a kneading barrel or the surface of a kneading screw of the kneading machine. This makes it possible to prevent metallic impurities from being mixed into the compound 3.

It is also preferred that the composition kneading operation in the present step [A-2b] is successively performed after completion of the preheating process in the step [A-2a] without having to cool the composition to below the softening point $T_2$ of the second organic component. This makes it possible to prevent occurrence of problems attendant on the cooling operation.

Examples of such problems include: the first and second organic components becoming susceptible to separation; the organic binder suffering from reduction in homogeneity; and the like, which would arise from the cooling of the preheated organic binder 2.

If necessary, the compound 3 thus obtained is pulverized into pellets (small masses) with a diameter of, e.g., about 1 to 10 mm. A pulverizing device such as a pelletizer or the like can be used in pelletizing the compound 3.

B: Molding Step

Next, the compound 3 is molded by an injection molding method. More specifically, the compound 3 is molded into specified shape and size by an injection molding machine to obtain a green body 4. In this case, depending on a cavity of a mold selected, it is possible to easily form a green body 4 having a complex and fine shape.

In other words, use of the injection molding method makes it possible to form the green body 4 into a shape close to a desired shape (namely, a near net shape). Therefore, it is possible to omit after processing and to reduce processing works to a great extent, which assists in simplifying the manufacturing process.

In particular, omission or reduction of the after processing offers great advantages, because hard-to-machine aluminum oxide powder having extremely high hardness is used as the raw material in the present invention.

The conditions of the injection molding method depend on the composition or particle size of the raw powder 1, the composition of the organic binder 2 and the blending quantity of the raw powder 1 and the organic binder 2 used. As an example, a material (composition) temperature is preferably in the range of about 80 to 200° C. and an injection molding pressure is preferably in the range of about 2 to 15 MPa (20 to 150 kgf/cm$^2$).

The geometry of the green body 4 to be formed is determined by taking into account shrinkage of the green body 4 which would occur in the subsequent debinding and sintering steps.

C: Surface Treatment Step

Next, resin particles are injected on the surface of the green body 4. In this connection, impurities adhering to the inner surface defining the cavity of the mold adhere to the surface of the green body 4 formed by the injection molding method.

These impurities are kept adhering to the surface of the translucent ceramic sintered body 6 obtained by debinding and sintering the green body. According to the prior art, these impurities inhibit incidence of light to a sintered body and adversely affect the translucency of the sintered body.

As a solution to this problem, the resin particles are injected on the surface of the green body 4 in the present embodiment. The resin particles thus injected impinge against the surface of the green body 4, thereby applying impact energy thereto. This makes it possible to perform a surface treatment by which to grind and remove the impurities present (adhering) on the surface of the green body 4.

As a result, it is possible to prevent the impurities from remaining on the surface o f the finally obtained translucent ceramic sintered body 6. Injection of the resin particles also makes it possible to remove burrs generated in the green body 4.

Use of the resin particles as particles injected on the surface of the green body 4 makes it possible to optimize the impact energy applied to the green body 4. In other words, since the resin particles are relatively lightweight and have relatively low hardness, it is possible to prevent the resin particles from applying unduly great impact energy to the green body 4.

This makes it possible to grind only the outermost surface layer of the green body 4 without adversely affecting geometry and surface smoothness of the green body 4. As a consequence, it is possible to obtain a translucent ceramic sintered body 6 with enhanced translucency, while avoiding notable reduction in dimensional accuracy of the translucent ceramic sintered body 6.

It is preferred that a constituent material of the resin particles used in this step is decomposable and removable in the below-mentioned debinding step. This kind of resin particles can be decomposed and removed in the below-mentioned debinding step, even if they adhere to the surface of the green body 4 when injected toward the surface of the green body 4.

Therefore, it is possible to prevent the resin particles from remaining in the translucent ceramic sintered body 6 and to prevent deterioration in translucency of the translucent ceramic sintered body 6.

From the viewpoint mentioned above, the constituent material of the resin particles includes, e.g., unsaturated polyester, polyethylene, polypropylene, polyamide (nylon), an acrylic resin, polystyrene and the like, one or more of which can be used independently or in combination.

It is preferred that the resin particles are mainly constituted of the unsaturated polyester. Since these resin particles exhibit optimal hardness relative to the hardness of the surface of the green body 4, it is possible to quite reliably grind only the outermost surface layer of the green body 4.

Owing to the fact that unsaturated polyester is easily decomposed and removed in the below-mentioned debinding step, it is possible to reliably prevent the resin particles from remaining in the translucent ceramic sintered body 6 even if they adhere to the green body 4 during the injection molding process.

An average particle size of the resin particles is preferably in the range of about 50 to 500 μm and more preferably in the range of about 70 to 400 μm. If the average particle size of the resin particles falls within the above-noted range, it is possible to reliably remove the impurities adhering to the surface of the green body 4, while preventing notable growth of the grinding marks formed on the surface of the green body 4 by impingement of the resin particles.

As a result, it is possible to prevent notable irregularities or impurities from remaining on the surface of the translucent ceramic sintered body 6 and to produce a translucent ceramic sintered body 6 with superior translucency. In addition, if the average particle size of the resin particles falls within the above-noted range, it is possible to optimize mass of the resin particles, i.e., the impact energy applied to the green body 4. This makes it possible to prevent serious reduction in dimensional accuracy of the green body 4.

D: Debinding Step

Next, the surface-treated green body 4 is subjected to a debinding process. The organic binder 2 present in the green body 4 is decomposed and removed by the debinding process, thereby providing a brown body 5. The green body 4 is gradually heated in the debinding step, at which time the organic binder 2 present in the green body 4 undergoes decomposition.

As mentioned earlier, the organic binder 2 includes the first organic component and the second organic component having a decomposition temperature lower than that of the first organic component. Use of the organic binder 2 including two components differing in decomposition temperature from each other ensures that decomposition and removal of the second organic component precedes decomposition and removal of the first organic component in the heating process.

By ensuring that the first and second organic components are decomposed and removed at different times, it is possible to prevent explosive decomposition and evaporation of the organic binder 2. Delayed decomposition of the first organic component makes it possible to prevent reduction in shape retention of the green body 4 in the debinding step.

This makes it possible to reliably debind the green body 4, while preventing generation of cracks, and to finally obtain a translucent ceramic sintered body 6 with high dimensional accuracy.

First decomposition and removal of the second organic component leaves tiny flow paths along traces of volatiles of the second organic component. Subsequently, volatiles of the first organic component pass through the flow paths. Therefore, the flow paths can be used in efficiently and reliably discharging the first organic component to the outside. In the manner described above, the organic binder 2 including the first and second organic components is reliably removed from the green body 4.

The flow paths are gradually filled from the central portions thereof as the brown body 5 is sintered in the below-mentioned sintering step. This makes it possible to reliably prevent the organic binder 2 or pores from remaining in the finally obtained sintered body 6.

It is preferred that a heating temperature (debinding temperature) of the green body 4 in the debinding step is preferably in the range of about 400 to 600° C. and more preferably in the range of about 450 to 550° C. By setting the debinding temperature within the above-noted range, it becomes possible to reliably debind the organic binder 2 having a general composition.

It is also possible to prevent explosive debinding of the green body 4, generation of cracks in the green body 4 and reduction in dimensional accuracy of the finally obtained brown body 5.

A heating time (debinding time) is suitably set depending on the debinding temperature and may be preferably in the range of about 1 to 30 hours and more preferably in the range of about 3 to 20 hours.

An atmosphere in which to perform the debinding process is preferably a vacuum (or depressurized) atmosphere or an atmosphere of inert gas such as a nitrogen gas, an argon gas or the like. This makes it possible to prevent degradation (alteration) of the raw powder 1 present in the green body 4.

The debinding process may be carried out in a plurality of divided steps for different purposes (e.g., for the purposes of shortening the debinding time and improving the shape retention). In this case, the debinding process may be carried out, e.g., in a pattern in which the green body 4 is debound at a low temperature during a first half thereof and at a high temperature during a second half thereof or in a pattern in which the low temperature debinding process and the high temperature debinding process are repeatedly carried out.

The organic binder 2 may partially remain in the brown body 5. The remaining organic binder 2 assists in enhancing the shape retention of the brown body 5 and can be removed in the below-mentioned sintering step.

E: Sintering Step

Next, the brown body 5 is subjected to a sintering process. Thus the brown body 5 is sintered to obtain a translucent ceramic sintered body 6, i.e., the bracket 10. By the sintering the brown body 5, the crystal grain boundaries existing in the brown body 5 disappear so that it is hard for light to be scattered by the crystal grain boundaries.

Therefore, the obtained translucent ceramic sintered body 6 increases the light translucency. In other words, by the sintering step, the obtained translucent ceramic sintered body 6 exhibits the light translucency.

A heating temperature (sintering temperature) of the brown body 5 is preferably in the range of about 1600 to 1900° C. and more preferably in the range of about 1700 to 1800° C. By setting the sintering temperature within the above-noted range, it becomes possible to reliably sinter the brown body 5 while preventing notable growth of crystal grains.

A heating time (sintering time) is suitably set depending on the sintering temperature and may be preferably in the range of about 0.5 to 8 hours and more preferably in the range of about 1 to 5 hours.

An atmosphere in which to perform the sintering process is preferably a vacuum (or depressurized) atmosphere or an atmosphere of reducing gas such as a hydrogen gas or the like. This makes it possible to prevent degradation (alteration) of the raw powder 1 which may be present in the brown body 5.

The atmosphere in which to perform the sintering process may be changed in the midst of the sintering process. For example, a depressurized atmosphere is first adopted and may be then switched to a reducing gas atmosphere in the midst of the sintering process.

Further, the sintering step may be performed in two or more divided steps. Furthermore, the sintering step is preferably performed in succession of the afore-mentioned debinding step. This makes it possible for the debinding step to serve as a pre-sintering step. Thus the brown body 5 can be more reliably sintered by preheating the brown body 5.

Now, a description will be made on an injection molding device (machine) used in the afore-mentioned molding step [B].

Figure 4:
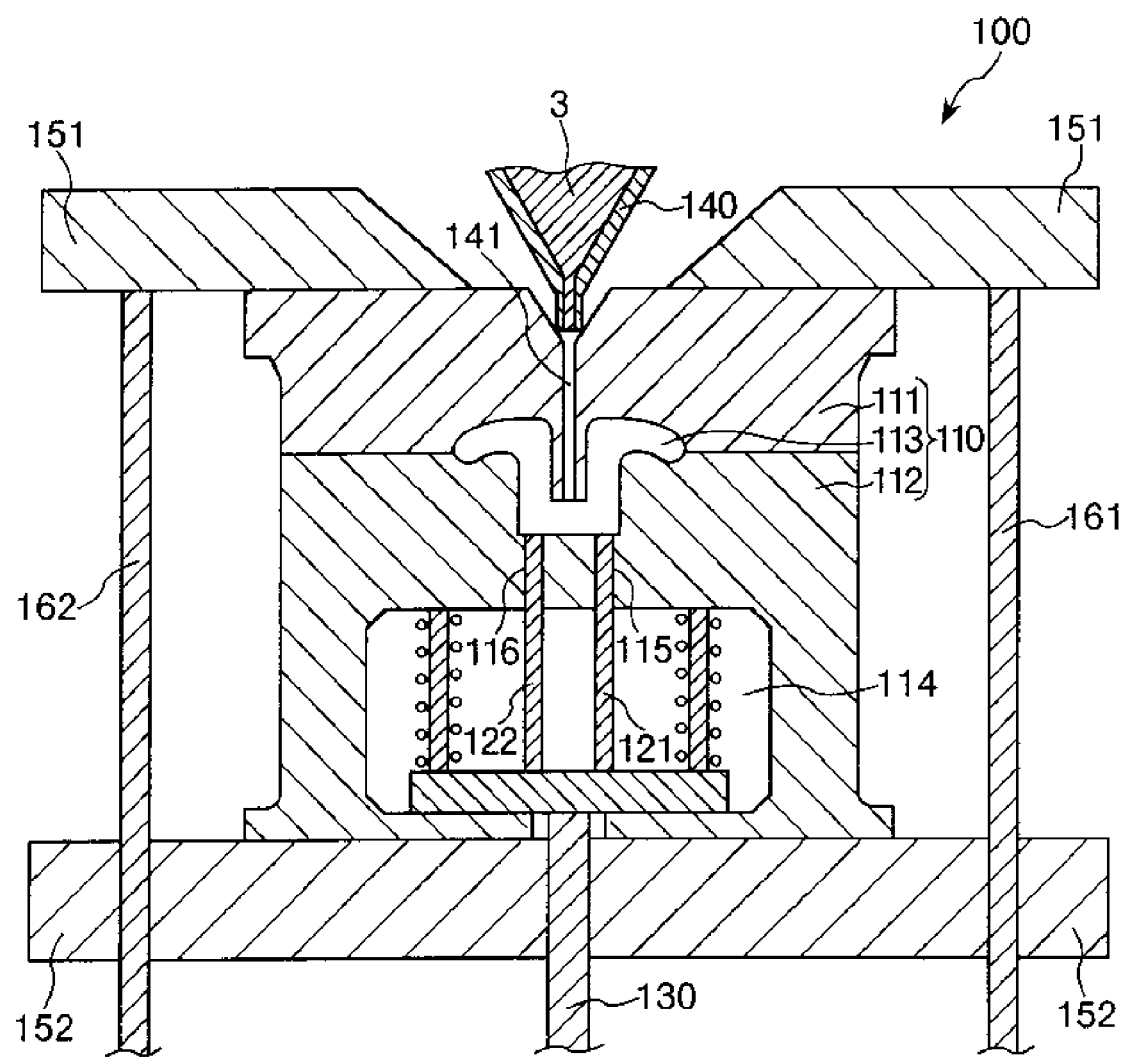
FIG. 4 is a vertical section view showing an injection molding device used in the method of manufacturing the translucent ceramic according to the present invention, with a mold thereof being in a closed state.
Figure 5:
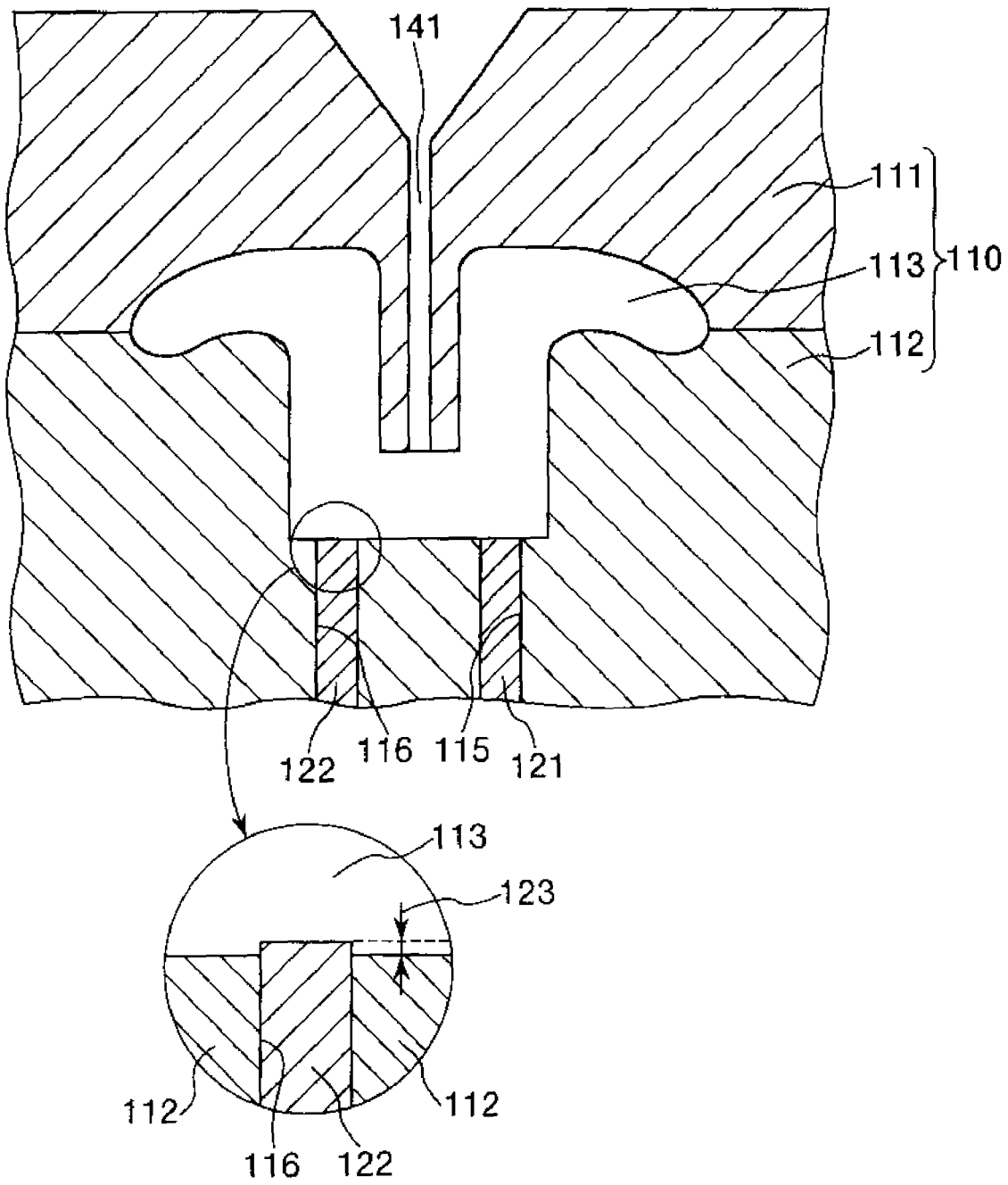
FIG. 5 is a partially enlarged view showing a cavity of the mold of the injection molding device shown in FIG. 4 and its vicinity.

FIG. 4 is a vertical section view showing an injection molding device used in the method of manufacturing the translucent ceramic according to the present invention, with a mold thereof being in a closed state. FIG. 5 is a partially enlarged view showing a cavity of the injection molding device shown in FIG. 4 and its vicinity.

Figure 6:
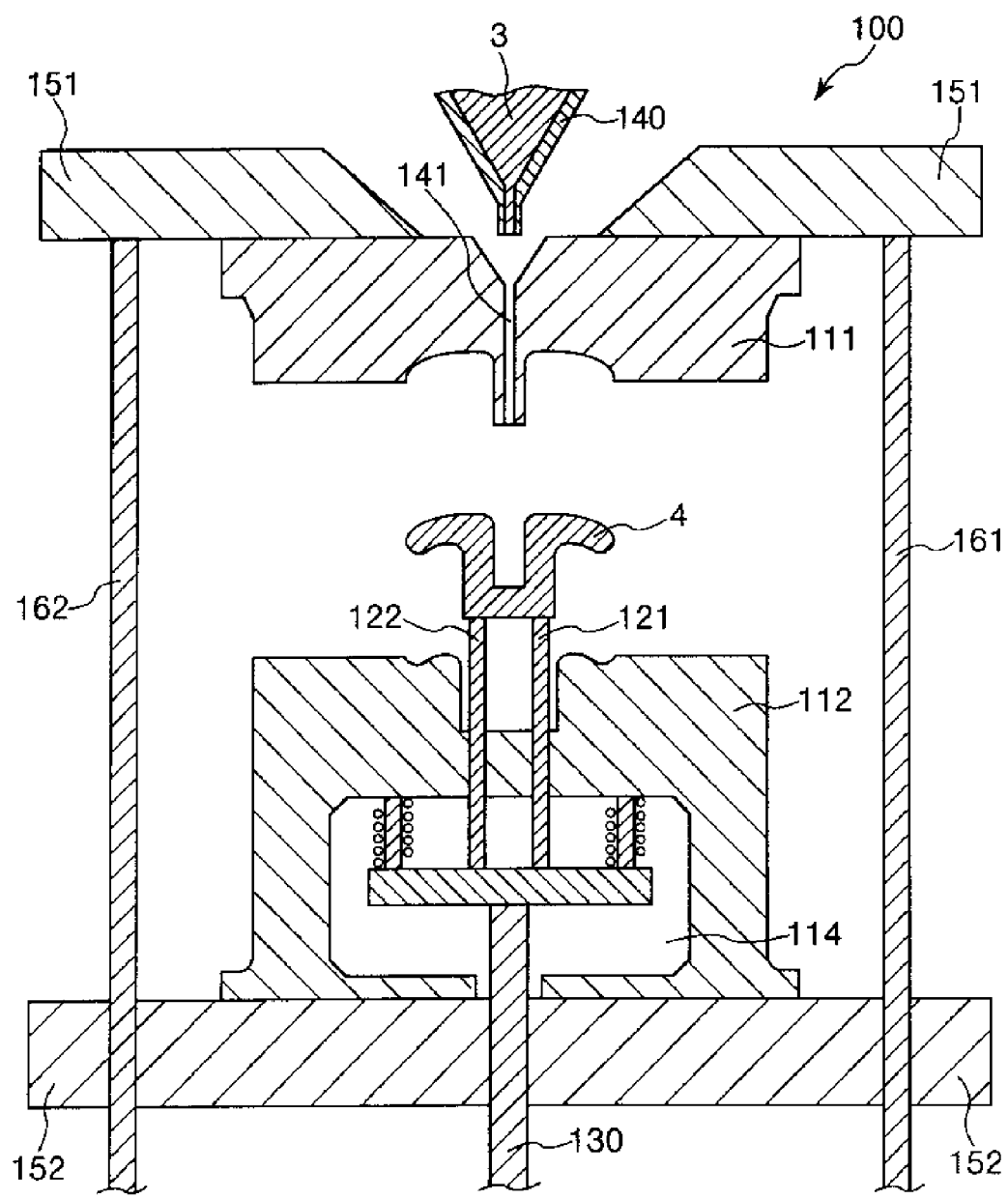
FIG. 6 is a vertical section view showing the injection molding device used in the method of manufacturing the translucent ceramic according to the present invention, with the mold thereof being in an open state.

FIG. 6 is a vertical section view showing the injection molding device used in the method of manufacturing the translucent ceramic according to the present invention, with the mold thereof being in an open state. In the following description, the upper side in FIGS. 4 through 6 will be referred to as "upper", with the lower side referred to as "lower".

The injection molding device 100 shown in FIG. 4 includes a mold 110 comprised of a first plate 111 and a second plate 112 openably closable together.

The injection molding device 100 further includes a support portion 151 for supporting the upper surface of the first plate 111 and a support portion 152 for supporting the lower surface of the second plate 112.

The support portion 152 is movable upwards and downwards and can move along a pair of rod-like guides 161 and 162 fixed to the support portion 151. As the support portion 152 makes up-and-down movement, a distance between the support portion 151 and the support portion 152 is changed, in response to which the mold 110 is opened and closed.

When the mold 110 is closed, a cavity 113 conforming to the shape of the green body 4 to be produced is defined in the parting surface (mold matching surface) between the first plate 111 and the second plate 112. A vertically extending flow path 141 is formed in the first plate 111 at a position corresponding to the cavity 113. The lower end of the flow path 141 is opened toward the cavity 113.

On the other hand, the upper end of the flow path 141 is opened in the upper surface of the first plate 111. A nozzle 140 through which to supply the compound 3 is connected to the upper opening of the flow path 141. The nozzle 140 injects the compound 3 into the cavity 113 through the flow path 141.

A green body 4 to which the shape of the cavity 113 is transferred can be formed by closing the mold 110 and then filling the compound 3 into the cavity 113.

Examples of a constituent material of the first and second plates 111 and 112 include dies steel, high-speed tool steel, cemented carbide, zirconia and the like.

The inner surface of the mold 110 defining the cavity 113 may be coated with titanium carbide (TiC), titanium nitride (TiN) or other materials.

In this regard, it is preferred that the inner surface of the mold 110 defining the cavity 113 is as smooth as possible. More specifically, a surface roughness Ra of the inner surface of the mold 110 defining cavity 113 is preferably 0.8 μm or less and more preferably 0.4 μm or less.

If the surface roughness Ra of the inner surface of the mold 110 falls within the above-noted range, the surface of the green body 4 becomes sufficiently smooth, eventually providing a sintered body 6 with a smooth surface. In terms of a wavelength of light, the surface roughness Ra of the inner surface of the mold 110 falling within the above-noted range is particularly effective in providing a translucent ceramic sintered body 6 that allows visible rays to sufficiently pass therethrough.

Therefore, the bracket 10 formed from the translucent ceramic sintered body 6 makes a color of teeth sufficiently visible, thereby providing good sensuousness.

It is preferred that the inner surface of the mold 110 defining the cavity 113 is as hard as possible. More specifically, the Vickers hardness HV of the inner surface of the mold 110 defining the cavity 113 is preferably 800 or more and more preferably 900 or more.

If the inner surface of the mold 110 defining the cavity 113 has high enough hardness as noted above, it is possible to restrain the inner surface of the mold 110 defining the cavity 113 from being damaged or worn out by friction with the compound 3 in the molding step. This makes it possible to restrain scars or the like left on the inner surface of the mold 110 defining the cavity 113 from being transferred to the green body 4.

Eventually, it is possible to restrain creation of irregularities on the surface of the translucent ceramic sintered body 6. Therefore, the translucent ceramic sintered body 6 with increased translucency can be obtained by ensuring that the hardness of the inner surface of the mold 110 defining the cavity 113 falls within the above-noted range.

The second plate 112 has an internal hollow portion 114 and two through-holes 115 and 116 through which the hollow portion 114 and the cavity 113 communicate with each other. Ejector pins 121 and 122 are slidably inserted into the through-holes 115 and 116, respectively.

Each of the ejector pins 121 and 122 is a rod-like member and is fixed to a drive unit 130 installed in the hollow portion 114. The ejector pins 121 and 122 are driven upwards and downwards by the drive unit 130.

When the mold 110 is in the closed state as shown in FIGS. 4 and 5, the ejector pins 121 and 122 are driven and controlled to assume a position in which the upper end surfaces thereof form a portion of a bottom surface of the inner surface of the mold 110 defining the cavity 113.

In contrast, when the mold 110 is in the open state as shown in FIG. 6, the ejector pins 121 and 122 are driven and controlled to assume a position in which they protrude into the cavity 113. Thus the green body 4 formed within the cavity 113 is pushed upwards by the ejector pins 121 and 122, thereby making it possible to take out the green body 4 from the cavity 113.

In this regard, it is preferred that the bottom surface of the inner surface of the mold 110 defining the cavity 113 and the upper end surfaces of the ejector pins 121 and 122 are flush with each other when the mold 110 is in the closed state. Depending on mechanical precision and accuracy, it may sometimes the case that a step difference is unintentionally created between the bottom surface of the inner surface of the mold 110 defining the cavity 113 and the upper end surfaces of the ejector pins 121 and 122.

A step difference 123 is shown in FIG. 5 as one example of the step difference created between the bottom surface of the inner surface of the mold 110 defining the cavity 113 and the upper end surfaces of the ejector pins 121 and 122. It is preferred that the step difference 123 is kept as small as possible, because it may leave irregularities (dimples (concave portions) in the present embodiment) on the surface of the green body 4 (or the translucent ceramic sintered body 6).

More specifically, the step difference 123 is preferably 0.05 mm or less and more preferably 0.03 mm or less. This ensures that irregularities possibly formed on the surface of the sintered body 6 by the ejector pins 121 and 122 is controlled small enough not to greatly affect the translucency of the translucent ceramic sintered body 6.

It is preferred that the ejector pins 121 and 122 are arranged in such positions as to correspond to the slit 40 or 50 of the bracket 10. When fixing the bracket 10 to the teeth, a wire extends through the slits 40 and 50.

If the ejector pins 121 and 122 are arranged in such positions as to correspond to the slit 40 or 50 as mentioned above, the irregularities formed on the surface of the translucent ceramic sintered body 6 by the step difference 123 are hidden behind a shadow of the wire. As a result, it is possible to prevent the irregularities from affecting the translucency of the bracket 10 and consequently marring the sensuousness of the bracket 10.

The bracket 10 (or the translucent ceramic sintered body 6) can be manufactured by the method described above.

With the above-described manufacturing method, magnesium oxide acts to restrain growth of the crystal grains of aluminum oxide in the process of sintering the brown body 5. As mentioned earlier, the aluminum oxide powder and the magnesium oxide powder are highly homogeneously dispersed in the compound 3. This assures homogeneous growth of the crystal grains of aluminum oxide, which makes it possible to prevent the crystal grains from growing into a notably great size.

The translucent ceramic sintered body 6 (or the bracket 10) having a uniform crystal grain size exhibits increased translucency, because transmission of light is hardly hindered by crystal grain boundaries. In addition, the translucent ceramic sintered body 6 (or the bracket 10) shows enhanced mechanical strength and increased hardness.

Since the green body 4 having a shape close to a desired shape can be obtained in the molding step as mentioned above, it is possible to omit after processing and to reduce processing works to a great extent, which assists in simplifying the manufacturing process.

Furthermore, since the impurities and the burrs remaining on the surface of the green body 4 can be removed in the surface treatment step, it becomes to make the surface of the green body 4 clean and smooth. This makes it possible to restrain (suppress) scattering and absorption of light on the surface of the green body 4 and to further increase the translucency of the translucent ceramic sintered body 6.

Owing to the fact that the green body 4 is efficiently and reliably debound in the debinding step, the translucent ceramic sintered body 6 does not contain any unnecessary matters such as residues of the organic binder 2 and pores. This makes it possible to prevent scattering of light, which would otherwise be caused by the unnecessary matters, and to prevent reduction in translucency of the translucent ceramic sintered body 6.

The translucent ceramic sintered body 6 thus manufactured is mainly constituted of polycrystalline alumina (i.e., polycrystalline aluminum oxide). With the present manufacturing method, it is therefore possible to manufacture a translucent ceramic sintered body with increased hardness, in which physical property of alumina prevail and the Mohs hardness of which is equal to about 9.

The translucent ceramic sintered body 6 exhibits bending stiffness close to that of sapphire (monocrystalline alumina). Therefore, the orthodontic member (bracket 10) constituted of this translucent ceramic sintered body 6 is less susceptible to cracks, fractures or other defects and enjoys increased reliability.

As set forth above, the translucent ceramic sintered body 6 has a compact structure containing little pores. More specifically, the present invention makes it possible to efficiently manufacture a translucent ceramic sintered body 6 whose relative density is 98% or more.

With the method of manufacturing the translucent ceramic according to the present invention, it is possible to manufacture a translucent ceramic sintered body 6 with increased transmittance, which shows 50% or more in a total light transmittance. When the orthodontic member formed from this translucent ceramic sintered body 6 is attached to the teeth, the orthodontic member (bracket 10) makes the color of the teeth fully visible, thereby realizing good sensuousness.

While the method of manufacturing the translucent ceramic and the orthodontic member using the translucent ceramic manufactured by the method in accordance with the present invention have been described with reference to one preferred embodiment, the present invention is not limited thereto.

For example, the orthodontic member using the translucent ceramic manufactured by the method according to the present invention is not limited to the orthodontic bracket having the shape described above and may be formed into any other shape. Furthermore, the present orthodontic member may be a member other than the orthodontic bracket.

If needed, an arbitrary step may be added to the method of manufacturing the translucent ceramic according to the present invention. For example, the green body, the brown body and the sintered body may be subjected to machining. In this case, the green body and the brown body can be machined with ease, because they show hardness lower than that of the sintered body.

It may also be possible to first manufacture a green body, a brown body and a sintered body, each of which has a shape corresponding to a plurality of orthodontic members, and then to sever them into a plurality of molded bodies, brown bodies and sintered bodies having a shape corresponding to the final orthodontic member.

In addition, the method of manufacturing the translucent ceramic according to the present invention is also capable of manufacturing other products such as an arc tube for discharge lamps mentioned earlier and the like.

EXAMPLES

1. Manufacture of Translucent Ceramic Sintered Body

Example 1

<1> First, a raw powder was prepared by mixing an aluminum oxide ($\alpha$-$Al_2O_3$) powder having an average particle size of 0.5 μm and a magnesium oxide powder having an average particle size of 0.2 μm. The blending ratio of the respective powders was set to ensure that a content of the magnesium oxide powder contained in the raw powder is equal to 0.05% by mass.

<2> Then, an organic binder was prepared by mixing: a first organic component including 26% by mass of polystyrene (having a softening point of 120° C. and a decomposition temperature of 590° C.) and 30% by mass of ethylene-vinyl acetate copolymer (having a softening point of 100° C. and a decomposition temperature of 475° C.); a second organic component including 28% by mass of paraffin wax (having a melting point of 55° C. and a decomposition temperature of 248° C.); and a plasticizer including 16% by mass of phthalic acid dibutyl (DBP).

<3> Next, a mixture (composition) was obtained by mixing the raw powder and the organic binder in a volume ratio of 58:42. Then, the mixture was preheated at a temperature of 120° C. for 10 minutes. The preheated mixture was put into a pressing kneader type kneading machine and kneaded at a temperature of 60° C. for 60 minutes, thereby obtaining a compound. The compound was pelletized by a pelletizer.

<4> Subsequently, the compound 3 thus obtained was injection-molded into a green body by an injection molding device under the molding conditions including a material (mixture) temperature of 150° C. and an injection pressure of 11 MPa (110 kgf/cm$^2$).

In this regard, it is to be noted that the injection molding device has a mold. The mold has an inner surface, a cavity defined by the inner surface, and ejector pins. Further, the inner surface includes a bottom surface. The inner surface of the mold of the injection molding device used at this time was formed from cemented carbide and had the Vickers hardness HV of 1000.

Furthermore, the inner surface had a surface roughness Ra of 0.6 μm. A step difference between the bottom surface of the inner surface and an end surface (upper surface in FIG. 5) of the ejector pins was 0.03 mm when the mold of the injection molding device was in a closed state.

<5> Next, unsaturated polyester particles having an average particle size of 150 μm were injected onto the surface of the green body thus obtained. A nozzle having an inner diameter Ø of 5 mm was used in injecting the unsaturated polyester particles. An injection pressure was 2 atm.

<6> The organic binder contained in the green body was debound under the debinding conditions including a debinding temperature of 520° C., a debinding time of 5 hours and a nitrogen gas atmosphere, thereby obtaining a brown body.

<7> Then, the brown body was sintered under the sintering conditions including a sintering temperature of 1800° C., a sintering time of 2.5 hours and a hydrogen gas atmosphere (with a hydrogen gas concentration of 100% by volume), thereby obtaining a translucent ceramic sintered body.

Example 2

A translucent ceramic sintered body was obtained in the same manner as in Example 1 except that the preheating temperature and the kneading temperature were changed to 125° C. and 70° C., respectively.

Example 3

A translucent ceramic sintered body was obtained in the same manner as in Example 1 except that the preheating temperature and the kneading temperature were changed to 175° C. and 90° C., respectively.

Example 4

A translucent ceramic sintered body was obtained in the same manner as in Example 2 except that polystyrene was replaced by polyethylene (having a softening point of 120° C. and a decomposition temperature of 490° C.).

Example 5

A translucent ceramic sintered body was obtained in the same manner as in Example 2 except that the content of the magnesium oxide powder contained in the raw powder was changed to 0.15% by mass.

Example 6

A translucent ceramic sintered body was obtained in the same manner as in Example 2 except that the content of the magnesium oxide powder contained in the raw powder was changed to 1% by mass.

Example 7

A translucent ceramic sintered body was obtained in the same manner as in Example 2 except that the content of the magnesium oxide powder contained in the raw powder was changed to 30% by mass.

Comparative Example 1

A translucent ceramic sintered body was obtained in the same manner as in Example 2 except that the preheating process was omitted.

Comparative Example 2

A translucent ceramic sintered body was obtained in the same manner as in Example 2 except that the preheating temperature was changed to 250° C.

Comparative Example 3

A translucent ceramic sintered body was obtained in the same manner as in Example 2 except that the kneading temperature was changed to 50° C.

Comparative Example 4

A translucent ceramic sintered body was obtained in the same manner as in Example 2 except that the preheating temperature and the kneading temperature were changed to 130° C.

Comparative Example 5

A translucent ceramic sintered body was obtained in the same manner as in Example 2 except that the organic binder is constituted of only the first organic component.

2. Evaluation of Sintered Body
2.1 Evaluation of Crystal Structure

With respect to the translucent ceramic sintered body obtained in each of the Examples 1 to 7 and each of the Comparative Examples 1 to 5, the translucent ceramic sintered body was cut to obtain a cross-section surface thereof. Then, a crystal structure of the cross-section surface was observed using an optical microscope and a scanning electron microscope.

The results of the observation showed that a size of each of particles included in the crystal structure was relatively uniform in the translucent ceramic sintered body obtained in each of the Examples 1 to 7. Few crystal structures of increased size and few pores were observed.

In contrast, a size of each of particles included in the crystal structure was uneven in the translucent ceramic sintered body obtained in each of the Comparative Examples 1 to 5. The crystal structure of increased size and pores were observed in some translucent ceramic sintered bodies.

2.2 Evaluation of Relative Density

With respect to the translucent ceramic sintered body obtained in each of the Examples 1 to 7 and each of the Comparative Examples 1 to 5, a specific gravity thereof was measured and a relative density thereof was calculated using a reference value derived from a composition of each of the raw powders. The relative density was evaluated according to the following evaluation criteria.

A: The relative density was 98% or more.
B: The relative density was equal to or greater than 96% but smaller than 98%.
C: The relative density was equal to or greater than 94% but smaller than 96%.
D: The relative density was smaller than 94%.

2.3 Evaluation of Dimensional Accuracy

With respect to the translucent ceramic sintered body obtained in each of the Examples 1 to 7 and each of the Comparative Examples 1 to 5, deviation in dimension from a desired shape was measured. Grade "A" was awarded in case where the deviation falls within a standard tolerance, but grade "D" was awarded in case where the deviation falls outside the standard tolerance.

2.4 Evaluation of Translucency

With respect to the translucent ceramic sintered body obtained in each of the Examples 1 to 7 and each of the Comparative Examples 1 to 5, total light transmittance was measured using the method specified in JIS K7361-1. The total light transmittance thus measured was evaluated according to the following evaluation criteria.

A: The total light transmittance was 50% or more.
B: The total light transmittance was equal to or greater than 40% but smaller than 50%.
C: The total light transmittance was equal to or greater than 30% but smaller than 40%.
D: The total light transmittance is smaller than 30%.

The results of evaluation conducted in sections 2.2, 2.3 and 2.4 are shown in Table 1.

TABLE 1

| | Conditions of manufacturing translucent ceramic | | | | | | | |
|---|---|---|---|---|---|---|---|---|
| | Raw powder | Organic binder | | Mixing and kneading conditions | | Evaluation results | | |
| | Content of MgO [% by mass] | First organic component | Second organic component | Preheating temperature [° C.] | Kneading temperature [° C.] | Relative density | Dimensional accuracy | Total light transmittance |
| Ex. 1 | 0.05 | PS + EVA | Paraffin wax | 120 | 60 | A | A | A |
| Ex. 2 | 0.05 | PS + EVA | Paraffin wax | 125 | 70 | A | A | A |
| Ex. 3 | 0.05 | PS + EVA | Paraffin wax | 175 | 90 | A | A | B |
| Ex. 4 | 0.05 | PE + EVA | Paraffin wax | 125 | 70 | B | A | B |
| Ex. 5 | 0.15 | PS + EVA | Paraffin wax | 125 | 70 | B | A | B |
| Ex. 6 | 1 | PS + EVA | Paraffin wax | 125 | 70 | B | A | C |
| Ex. 7 | 30 | PS + EVA | Paraffin wax | 125 | 70 | B | A | C |
| Comp. Ex. 1 | 0.05 | PS + EVA | Paraffin wax | — | 70 | C | A | D |

TABLE 1-continued

Conditions of manufacturing translucent ceramic

| | Raw powder | Organic binder | | Mixing and kneading conditions | | Evaluation results | | |
|---|---|---|---|---|---|---|---|---|
| | Content of MgO [% by mass] | First organic component | Second organic component | Preheating temperature [° C.] | Kneading temperature [° C.] | Relative density | Dimensional accuracy | Total light transmittance |
| Comp. Ex. 2 | 0.05 | PS + EVA | Paraffin wax | 250 | 70 | C | D | C |
| Comp. Ex. 3 | 0.05 | PS + EVA | Paraffin wax | 125 | 50 | D | D | C |
| Comp. Ex. 4 | 0.05 | PS + EVA | Paraffin wax | 130 | 130 | C | D | C |
| Comp. Ex. 5 | 0.05 | PS + EVA | — | 125 | 70 | D | D | D |

PS: Polystyrene,
PE: Polyethylene,
EVA: Ethylene-vinyl acetate copolymer

As can be seen in Table 1, the relative density of the translucent ceramic sintered body obtained in each of the Examples 1 to 7 was higher than that of the translucent ceramic sintered body obtained in each of the Comparative Examples 1 to 5. Presumably, this is because the translucent ceramic sintered body obtained in each of the Examples 1 to 7 are relatively compact and have a relatively small number of pores.

Furthermore, the total light transmittance of the translucent ceramic sintered body obtained in each of the Examples 1 to 7 was equal to or greater than that of the translucent ceramic sintered body obtained in each of the Comparative Examples 1 to 5.

Presumably, this is because the translucent ceramic sintered body obtained in each of the Examples 1 to 7 has uniform and compact crystal structures, which makes it hard for the light to be scattered by the crystal grain boundaries and consequently increases the light translucency. Accordingly, it can be said that the translucent ceramic sintered body obtained in each of the Examples 1 to 7 are suitable for use as, e.g., orthodontic members with good sensuousness.

The translucent ceramic sintered body obtained in each of the Examples 1 to 7 shown high dimensional accuracy. Presumably, this is because the compound has increased homogeneity and an optimized viscosity, which makes it possible to improve the shape retention in the molding step and to restrain change in shape in the debinding step.

In each of the Examples 1 to 7, the translucent ceramic sintered body having a relatively low content of magnesium oxide exhibited higher translucency than the translucent ceramic sintered body having a relatively high content of magnesium oxide.

The reason is presumed to be that the increase in the content of magnesium oxide leads to easier reaction of aluminum oxide and magnesium oxide, which in turn produces a large quantity of compounds such as spinel ($MgAl_2O_4$) and the like and eventually reduces the light transmittance.

What is claimed is:

1. A method of manufacturing a translucent ceramic, the method comprising:
   mixing a raw powder, a plasticizer and an organic binder and kneading them to obtain a compound, wherein the raw powder contains an aluminum oxide powder and a magnesium oxide powder, the plasticizer contains phthalate ester consisting of phthalic acid dibutyl, and the organic binder contains a first organic component and a second organic component of which decomposition temperature is lower than a decomposition temperature of the first organic component, wherein the first organic component is polystyrene and ethylene-vinyl acetate copolymer, and a content of the polystyrene and the ethylene-vinyl acetate copolymer is 26:30;
   molding the compound in a predetermined shape by an injection molding method to obtain a green body;
   debinding the organic binder contained in the green body to obtain a brown body; and
   sintering the brown body to obtain a sintered body of the translucent ceramic;
   wherein the kneading step is carried out at a temperature in the range of 60 to 120° C. after the raw powder, the plasticizer and the organic binder are preheated at a temperature in the range of 100 to 175° C.

2. The method as claimed in claim 1, wherein a content of the magnesium oxide powder contained in the raw powder is in the range of 0.01 to 0.15% by mass.

3. The method as claimed in claim 1, wherein a content of the raw powder in the mixing step is in the range of 30 to 70% by volume.

4. The method as claimed in claim 1, wherein the second organic component includes a paraffin wax.

5. The method as claimed in claim 1, wherein a content of the second organic component contained in the organic binder is in the range of 10 to 50% by mass.

6. The method as claimed in claim 1, wherein the kneading step is successively carried out without having to cool the raw powder and the organic binder to below the range of 60 to 120° C. after completion of the preheating.

7. The method as claimed in claim 1, wherein the debinding step is carried out under debinding conditions that a debinding temperature is in the range of 400 to 600° C. and a debinding time is in the range of 1 to 20 hours.

8. The method as claimed in claim 1, wherein the sintering step is carried out under sintering conditions that a sintering temperature is in the range of 1600 to 1900° C. and a sintering time is in the range of 0.5 to 8 hours.

9. The method as claimed in claim 1 further comprising subjecting the green body having a surface to a surface treatment between the molding step and the debinding step, wherein the surface treatment is carried out by injecting resin particles onto the surface of the green body.

10. The method as claimed in claim 9, wherein the resin particles are decomposable in the debinding step.

11. The method as claimed in claim 9, wherein an average particle size of the resin particles is in the range of 50 to 500 gm.

12. The method as claimed in claim 9, wherein the resin particles are constituted of unsaturated polyester as a main component thereof.

13. The method as claimed in claim 9, wherein the subjecting step is carried out under an injection pressure of 2 atm.

14. The method as claimed in claim 1, wherein the injection molding method uses a mold, the mold has an inner surface and a cavity defined by the inner surface, and Vickers hardness HV of the inner surface of the mold is 800 or more.

15. The method as claimed in claim 14, wherein a surface roughness Ra of the inner surface of the mold is 0.8 μm or less.

16. The method as claimed in claim 14, wherein the mold has the cavity having a predetermined shape, and ejector pins provided for insertion into and extraction from the cavity and configured to push out the green body formed by the mold from the cavity, wherein each of the ejector pins has a surface to push the green body and the inner surface of the mold includes a bottom surface, wherein in a state that the mold is closed, a step difference between the bottom surface of the inner surface of the mold and the surface of each of the ejector pins is 0.05 mm or less.

* * * * *